(12) United States Patent
Noyes et al.

(10) Patent No.: US 11,737,660 B2
(45) Date of Patent: Aug. 29, 2023

(54) ARTICULATING CANNULA WITH ENDOSCOPE ATTACHMENT

(71) Applicant: ResnENT, LLC, Bloomington, IL (US)

(72) Inventors: Willard S. Noyes, Bloomington, IL (US); Benjamin Joseph Gray, Portland, ME (US)

(73) Assignee: RESNENT, LLC, Bloomington, IL (US)

( * ) Notice: Subject to any disclaimer, the term of this patent is extended or adjusted under 35 U.S.C. 154(b) by 0 days.

(21) Appl. No.: 17/853,308

(22) Filed: Jun. 29, 2022

(65) Prior Publication Data

US 2022/0409017 A1 Dec. 29, 2022

Related U.S. Application Data

(60) Provisional application No. 63/216,209, filed on Jun. 29, 2021.

(51) Int. Cl.
| | | |
|---|---|---|
| *A61B 1/005* | (2006.01) | |
| *A61B 1/00* | (2006.01) | |
| *A61B 1/018* | (2006.01) | |
| *A61M 25/10* | (2013.01) | |

(52) U.S. Cl.
CPC .......... *A61B 1/0057* (2013.01); *A61B 1/0055* (2013.01); *A61B 1/00066* (2013.01); *A61B 1/00082* (2013.01); *A61B 1/00101* (2013.01); *A61B 1/00105* (2013.01); *A61B 1/018* (2013.01); *A61M 25/10184* (2013.11)

(58) Field of Classification Search
CPC ............ A61B 1/00066; A61B 1/00082; A61B 1/00101; A61B 1/00105; A61B 1/0055; A61B 1/0057; A61B 1/018; A61B 1/005
See application file for complete search history.

(56) References Cited

U.S. PATENT DOCUMENTS

| | | | |
|---|---|---|---|
| 5,549,542 | A | 8/1996 | Kovalcheck |
| 9,107,574 | B2 | 8/2015 | Goldfarb et al. |
| 9,655,639 | B2 | 5/2017 | Mark |
| 10,137,285 | B2 | 11/2018 | Jenkins et al. |
| 10,512,391 | B2 | 12/2019 | Noyes |
| 10,639,462 | B2 | 5/2020 | Matlock et al. |
| 2002/0045915 | A1 | 4/2002 | Balceta et al. |
| 2010/0087811 | A1 | 4/2010 | Herrin et al. |

(Continued)

FOREIGN PATENT DOCUMENTS

EP  3612077 A1  2/2020

OTHER PUBLICATIONS

International Search Report and Written Opinion dated Oct. 26, 2022 for International Application No. PCT/US2022/035541.

*Primary Examiner* — Aaron B Fairchild

(74) *Attorney, Agent, or Firm* — Sheppard, Mullin, Richter & Hampton LLP

(57) ABSTRACT

An articulating cannula assembly is described. The articulating cannula assembly includes: a hand piece; a proximal housing situated above the hand piece; a cannula distally extending from the proximal housing, the cannula including an articulating segment; and a trigger that, when actuated, extends or contracts the articulating segment. The proximal housing can removably couple to the hand piece. The proximal housing can include an endoscope attachment structure for removably securing a proximal portion of an endoscope.

20 Claims, 21 Drawing Sheets

(56) References Cited

U.S. PATENT DOCUMENTS

| | | | |
|---|---|---|---|
| 2010/0280449 A1* | 11/2010 | Alvarez | A61B 34/71 606/1 |
| 2014/0316434 A1 | 10/2014 | Simaan et al. | |
| 2017/0231474 A1 | 8/2017 | Saadat et al. | |
| 2018/0326144 A1 | 11/2018 | Truckai | |

* cited by examiner

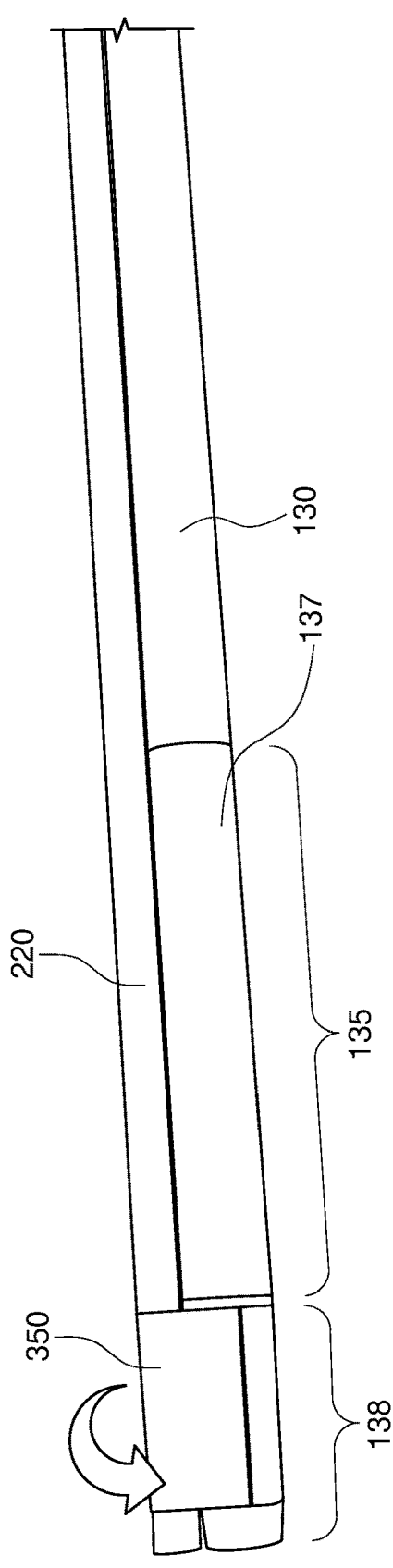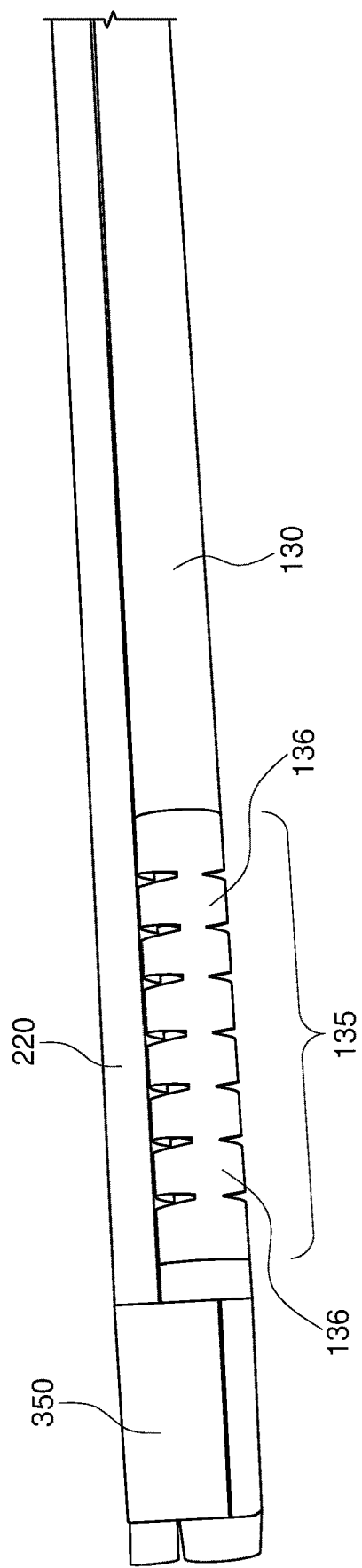

ARTICULATING CANNULA WITH ENDOSCOPE ATTACHMENT

CROSS-REFERENCE TO RELATED APPLICATIONS

The present application claims the benefit of U.S. Provisional Patent Application No. 63/216,209 filed on Jun. 29, 2021 and titled "Articulating Cannula with Endoscope Attachment," which is incorporated herein by reference in its entirety.

BACKGROUND

Endoscopes are illuminated tubular instruments with eyepieces, cameras, or camera chips that are used to look inside a body cavity in procedures called an endoscopy. During performance of a medical procedure with an instrument that is inserted within a patient's body cavity, endoscopes may be used to visualize the medical instrument and body cavity during the procedure. For example, the endoscope may be used to allow the physician to view tissue or other matter within a cavity or anatomic space in a patient while using suction or grasping forceps to remove tissue from the space.

In procedures that utilize medical instruments in combination with endoscopes, the endoscope is typically a rigid or flexible tool that is manipulated separately from the medical instrument. During the procedure, medical personnel hold and guide the rigid or flexible endoscope with one hand and the instrument used to treat the patient with the other hand. Depending on the anatomic space to be visualized, physicians will use either a rigid or flexible endoscope. For example, pulmonologists and gastroenterologists use flexible endoscopes and orthopedic surgeons typically use rigid endoscopes, whereas otolaryngologists use either rigid or flexible scopes depending on the surgical application. When using endoscopes with other surgical instrumentation within a confined space, there is often interference between the endoscope and instrument when trying to manipulate within the same anatomic space. This is sometimes referred to as "sword fighting" and can make surgeries technically more difficult and sometimes require another incision or access port to overcome. This is particularly true in orthopedic arthroscopy.

Current implementations of rigid endoscopes have significant limitations with respect to visualizing the patient's body cavity during a procedure. The surgeon is often handicapped by the rigidity of the endoscope and the angle of visualization when trying to perform tasks in areas difficult to reach with instruments. The surgeon is handicapped even with the available angled rigid scope visualization. In addition, especially in pediatric cases, there is simply not enough room to insert multiple instruments in a nasal passage or sinus opening at the same time. Further, angled rigid scope visualization often distorts the surgeon's perspective and is cumbersome to use in conjunction with secondary instruments such as forceps in a small cavity.

Likewise, current implementations of flexible endoscopes present their own set of problems. In some current flexible endoscopic systems on the market, a tool is required to be threaded through a tiny instrument channel incorporated within the length of a flexible endoscope. In such systems, the size of the tool is limited to the diameter of the endoscopic channel, and thus greatly limits the tool options available for endoscopic tissue manipulation. Externally attaching a flexible endoscope to a surgical instrument or device is difficult because the endoscope is difficult to stabilize, the endoscope hangs off the back of the instrument, and the endoscope does not connect or transfer easily from one instrument to another. Use of currently available flexible endoscopes requires two hands: one hand to manipulate the tip flexion and another hand to stabilize the tip of the flexible shaft as it enters an anatomic opening.

Endoscope visualization is often impaired by surface smudging and clouding of the lens from bodily fluids or tissue debris. Attempts have been made by multiple medical device manufactures over the years to utilize irrigation/suction cannulas and pump/suction systems to clear the lens of such debris. These systems are cumbersome, expensive, and often inadequate in performing their intended purpose. These types of systems have been designed primarily for rigid scopes and not for flexible scopes. Certain flexible scopes such as bronchoscopes and colonoscopes have channel lumens capable of suction and irrigation, but flexible endoscopes without inner channels have no means by which to clear the lens of debris.

With the advent of robotic surgery, many types of articulating surgical forceps have been devised to use through surgical ports under endoscopic visualization. Robotic surgery however is expensive and impractical for many surgical procedures. Further, the introduction of an endoscope and one or more instruments into an anatomical space generally requires more than one surgical port for access. This requires longer or multiple incisions, increases scarring, surgical time, and patient discomfort while making it more difficult to perform surgeries in an office-based setting.

SUMMARY

Some implementations described herein are directed to an articulating cannula assembly. The assembly can have a removable endoscope attachment.

In one embodiment, an articulating cannula assembly, comprises: a hand piece; a proximal housing situated above the hand piece; a cannula distally extending from the proximal housing, the cannula comprising an articulating segment; and a trigger that, when actuated, extends or contracts the articulating segment.

In some implementations, the proximal housing is to removably couple to the hand piece.

In some implementations, the hand piece is a balloon pump hand piece comprising a connection port to fluidically couple to a balloon catheter; the balloon pump handpiece comprises a control to inflate a distal balloon of the balloon catheter; and a top portion of the balloon pump hand piece comprises a mechanism to removably couple to the proximal housing.

In some implementations, the proximal housing comprises a port that connects to the cannula; the port is configured to receive the distal balloon of the balloon catheter; and after the distal balloon is received at the port, it is to be passed through the cannula.

In some implementations, one of the hand piece or the proximal housing comprises a T-shaped attachment structure; one of the hand piece or the proximal housing comprises a T-track; and the hand piece is removably coupled to the proximal housing by sliding the T-shaped attachment structure in the T-track.

In some implementations, the proximal housing comprises a first port and a second port that connect to the cannula; and the first port is to receive a first instrument that is passed through the cannula; and the second port is to receive a second instrument that is passed through the cannula.

In some implementations, the articulating cannula assembly further comprises: a first tube that connects the first port to the cannula, and passes through at least a portion of the cannula; and a second tube that connects the second port to the cannula, and passes through at least a portion of the cannula, where the first instrument is to be passed through the first tube, and the second instrument is to be passed through the second tube.

In some implementations, the first tube and the second tube separately terminate within the cannula or after a distal end of the cannula. In some implementations, the first tube and the second tube merge into a single channel within the cannula.

In some implementations, the first port and the second port are situated on opposite sides of the proximal housing.

In some implementations, the proximal housing comprises a third port that connects to the cannula, the third port to receive a third instrument that is passed through the cannula, the first port and the second port are situated on left and right sides of the proximal housing, and the third port is situated on a rear side of the proximal housing.

In some implementations, the proximal housing comprises a first port that connects to the cannula, the first port situated on a rear side of the proximal housing and to receive one or more instruments that are passed through the cannula.

In some implementations, the cannula further comprises a rotatable segment distal to the articulating segment, the rotatable segment to rotate independent of a remainder of the cannula.

In some implementations, the articulating segment comprises multiple notches that widen or close when the trigger is actuated. In some implementations, the articulating cannula assembly further comprises: a pulley incorporated into the proximal housing; and one or more wires coupling the articulating segment to the pulley.

In some implementations, the articulating segment comprises a flexible coating disposed over the multiple notches.

In some implementations, the proximal housing comprises a first endoscope attachment structure for removably securing a proximal portion of an endoscope.

In some implementations, the first endoscope attachment structure comprises an open channel with side walls and a distal hole that extends from a distal end of the open channel to a distal end of the proximal housing; and the endoscope is removably secured to the first endoscope attachment structure by threading a shaft of the endoscope through the distal hole and securing the proximal portion of the endoscope within the open channel.

In some implementations, the articulating cannula assembly further comprises a second endoscope attachment structure for securing an exterior of the cannula to a shaft of the endoscope.

In some implementations, the second endoscope attachment structure is incorporated into a distal portion of the cannula.

In some implementations, the cannula further comprises a rotatable segment distal to the articulating segment, the rotatable segment comprising the second endoscope attachment structure, and the rotatable segment to rotate independent of a remainder of the cannula.

In one embodiment, an articulating cannula assembly comprises a proximal housing including a coupling mechanism to removably couple to a top portion of a hand piece; a cannula distally extending from the proximal housing, the cannula comprising an articulating segment; and a trigger that, when actuated, extends or contracts the articulating segment.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIG. 11 shows a distal end of an endoscope shaft secured to a distal end of a cannula of an articulating cannula assembly, the cannula including an articulating segment covered by a flexible coating, in accordance with some implementations of the disclosure.

FIG. 12 shows a distal end of an endoscope shaft secured to a distal end of a cannula of an articulating cannula assembly, the cannula including an exposed articulating segment, in accordance with some implementations of the disclosure.

Figure 1:
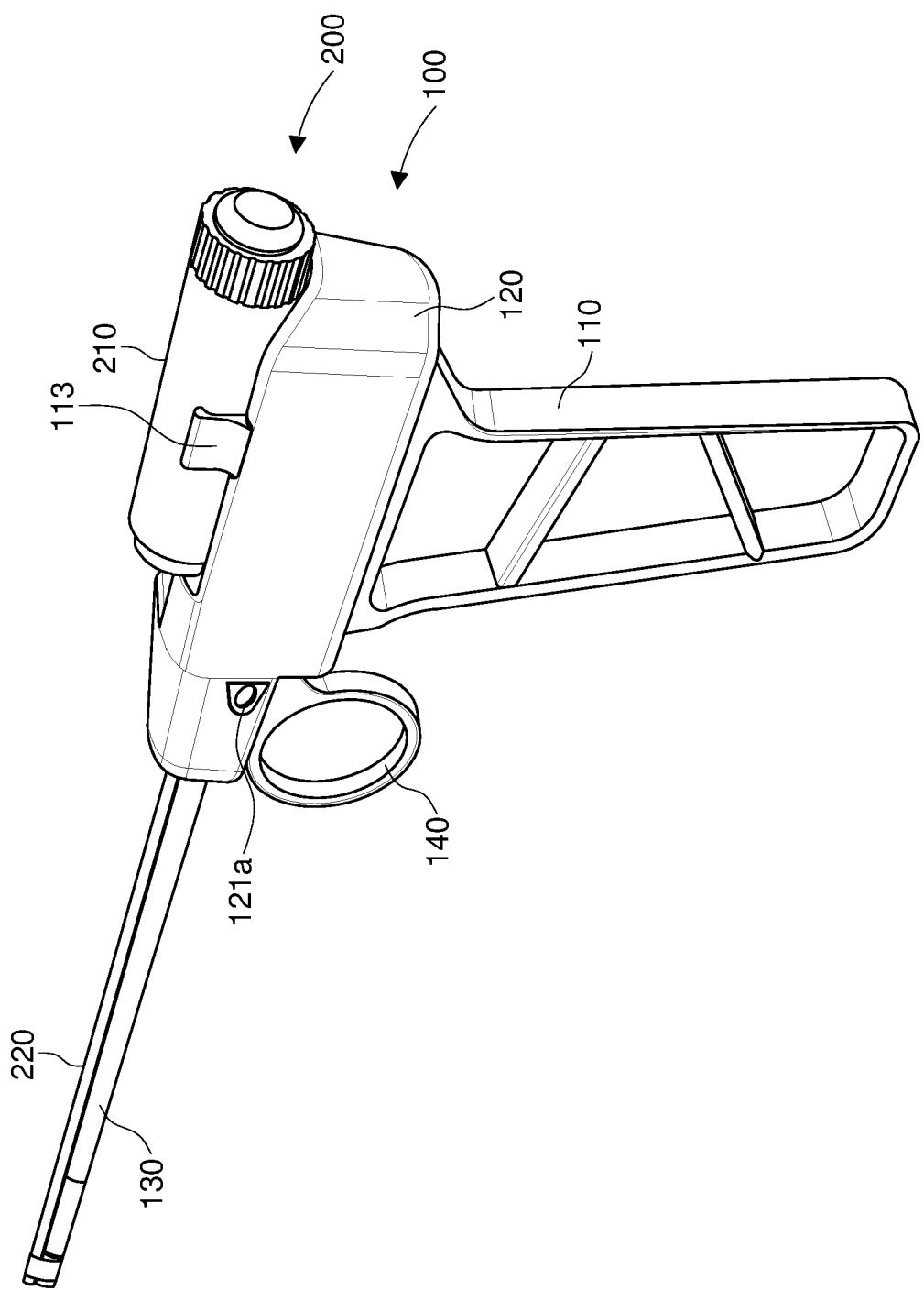
FIG. 1 shows a left side perspective view of an articulating cannula assembly with a coupled endoscope, in accordance with some implementations of the disclosure.
Figure 2:
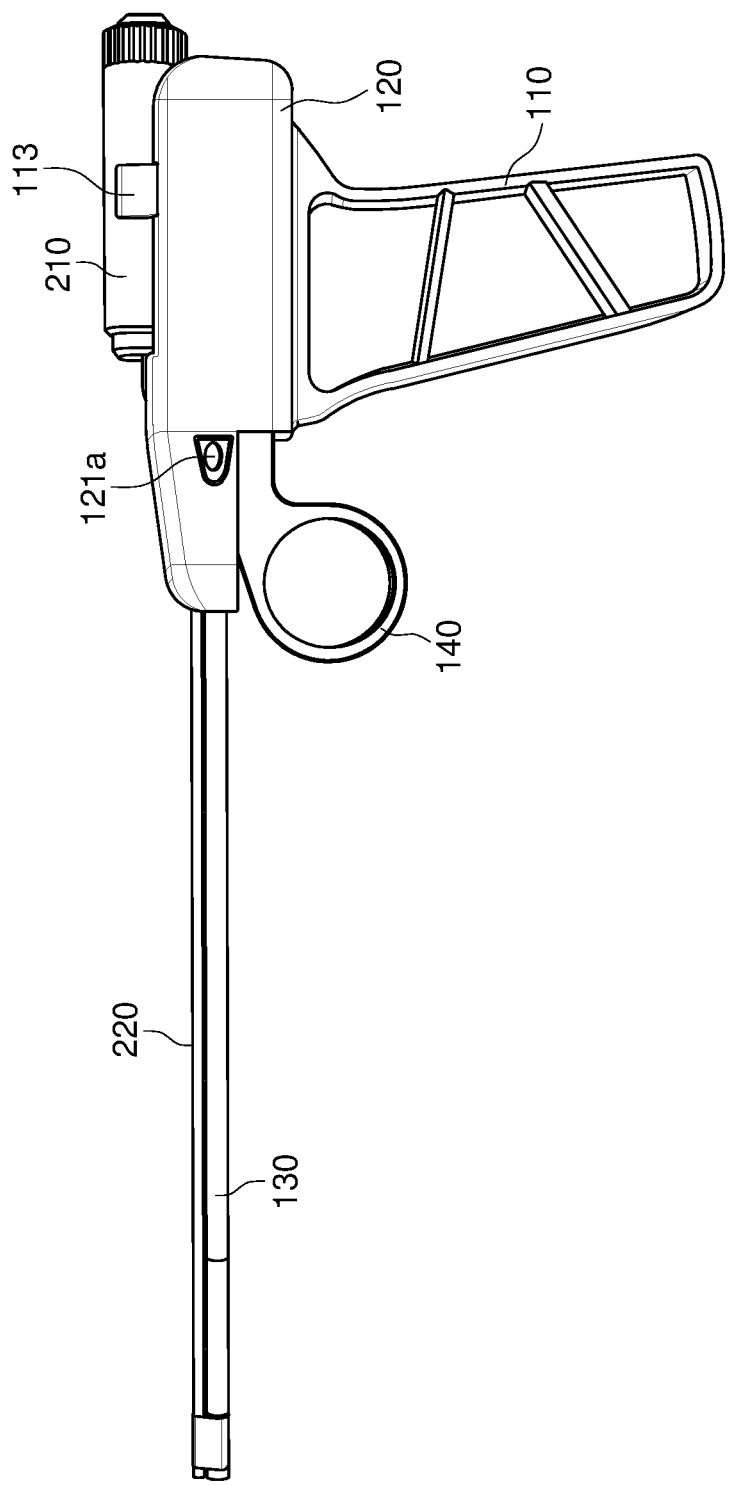
FIG. 2 shows a left side view of an articulating cannula assembly, with a coupled endoscope, in accordance with some implementations of the disclosure.
Figure 3:
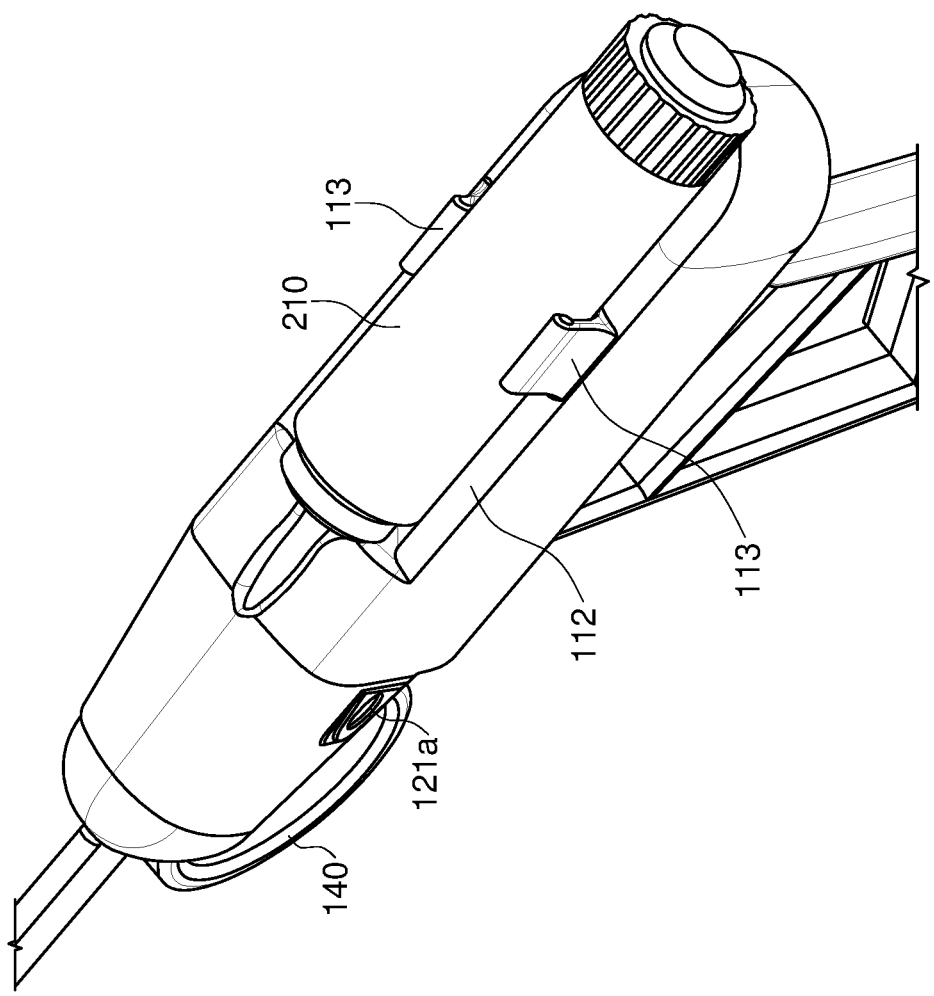
FIG. 3 shows a top side perspective view of an articulating cannula, including a mechanism for coupling the endoscope, in accordance with some implementations of the disclosure.
Figure 4:
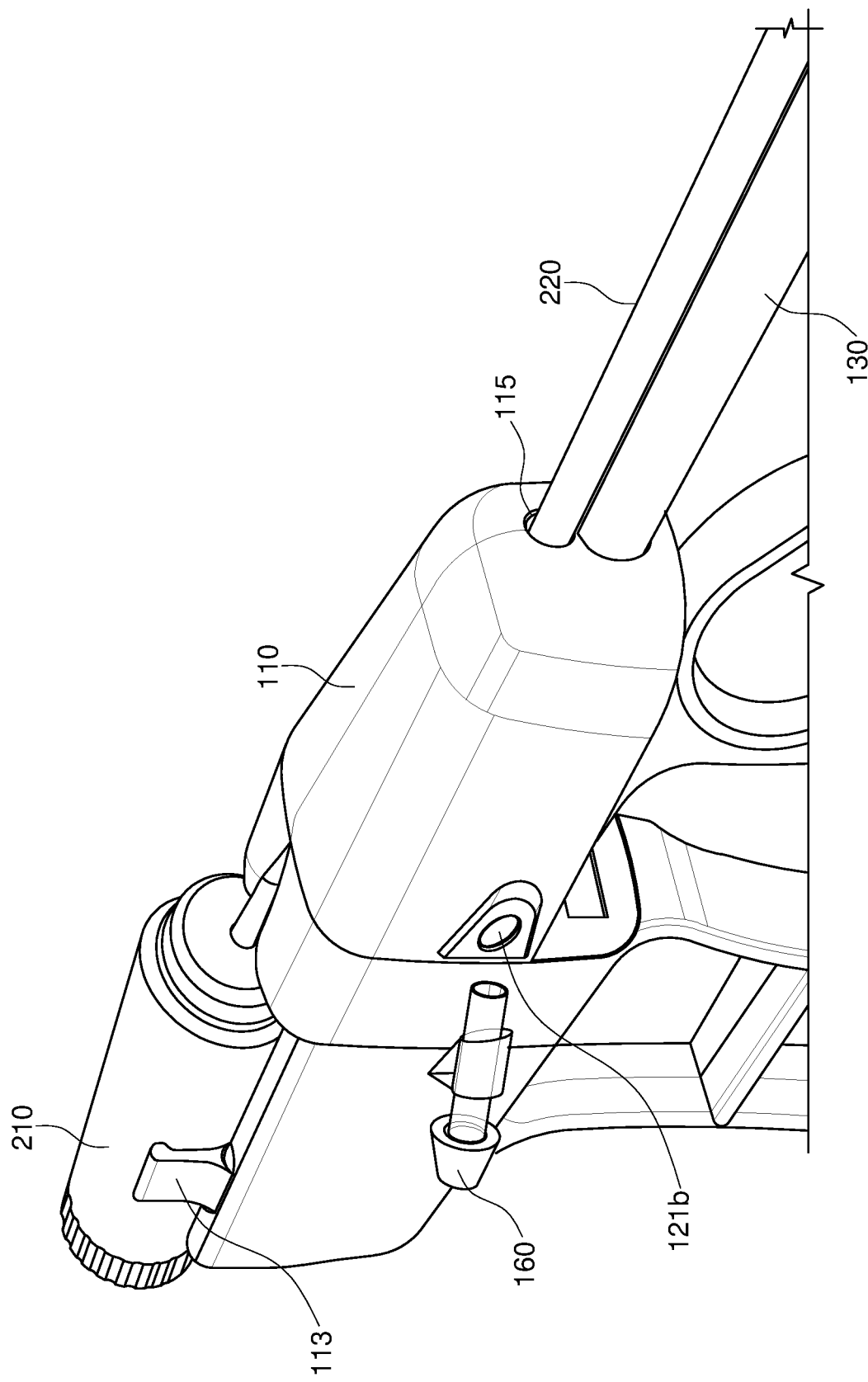
FIG. 4 shows a right side perspective view of an articulating cannula assembly with a coupled endoscope, including a suction adapter that can couple to a port of the assembly, in accordance with some implementations of the disclosure.
Figure 5:
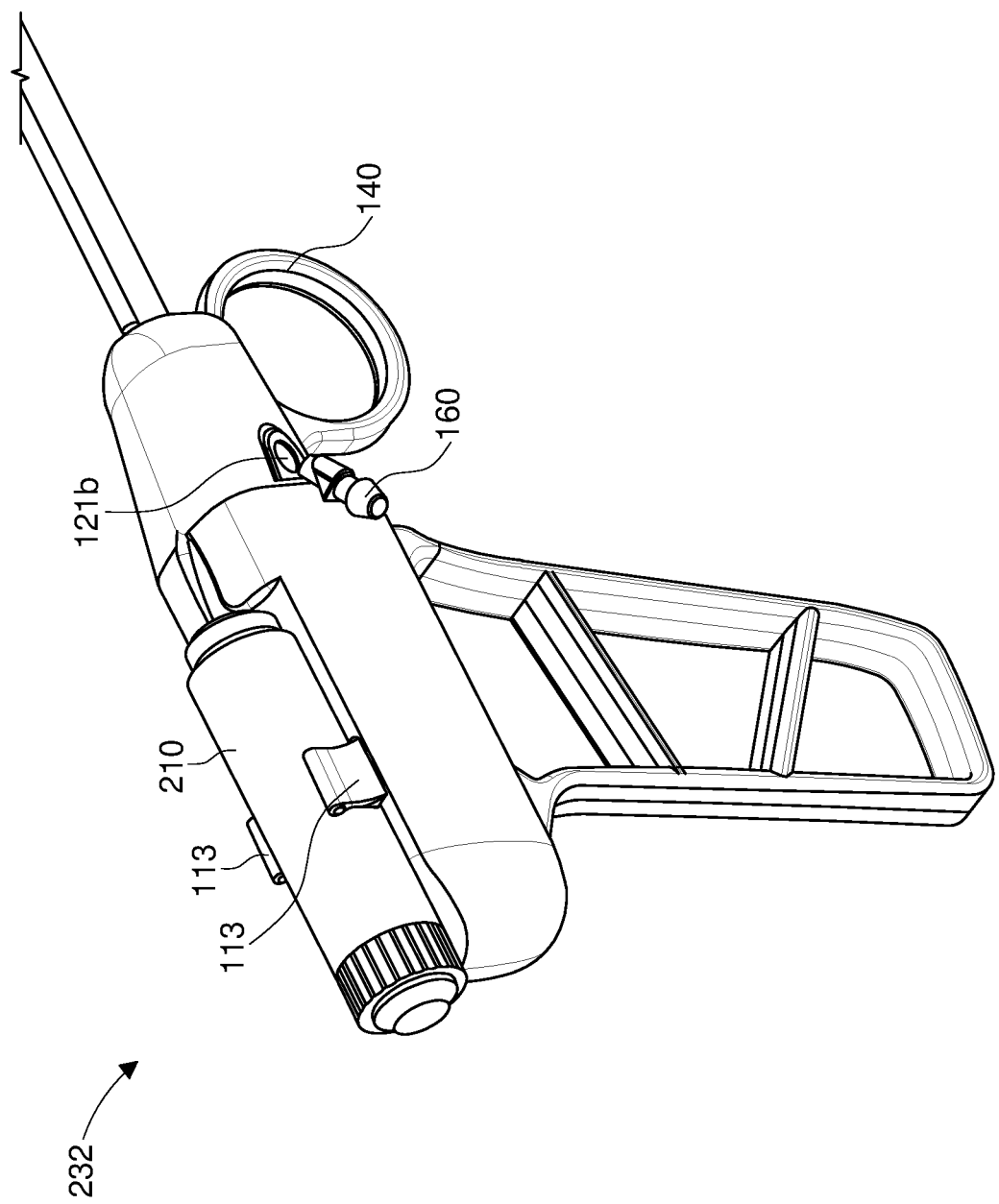
FIG. 5 shows a right side perspective view of an articulating cannula assembly with a coupled endoscope, including a suction adapter that can couple to a port of the assembly, in accordance with some implementations of the disclosure.

The figures are not exhaustive and do not limit the disclosure to the precise form disclosed.

DETAILED DESCRIPTION

Attaching an endoscope to articulating and non-articulating instruments or cannulas would decrease the number of free-standing surgical devices competing for space within the same anatomical space. In orthopedics for instance, current arthroscopic techniques use a multiple port approach using only rigid endoscopes for visualization. By attaching an endoscope to a surgical instrument or hollow cannula, the number of access ports required would be decreased and potentially allow for single port surgery and better patient outcomes. In yet other areas of surgical specialty, using a flexible or hybrid endoscope attached to an articulating cannula or instrument would allow for minimized instrumentation, increased visualization, and easier tissue manipulation within a confined space and therefore lead to better, simpler, cheaper, more efficient, and better tolerated surgical procedures and outcomes.

To this end, FIGS. 1-20, depict an articulating cannula assembly 100, in accordance with some implementations of the disclosure. FIGS. 1-14 show various external views of the articulating cannula assembly 100, and FIGS. 15-20 show various internal or cross-sectional views of the articulating cannula assembly 100. The assembly 100 may be utilized in various endoscopic applications, including applications that require dilation or instrumentation within a human cavity, such as the paranasal sinus, trachea, esophagus, bladder, uterus, abdomen, joint space, or other anatomic location. For example, the assembly 100 may function as an esophageal dilator or as a tracheal dilator. Assembly 100 could also be used during single portal arthroscopy. Additionally, the assembly 100 may be used in trans-nasal, transoral, urologic, neurosurgical, and general surgery/robotic procedures.

The assembly 100 includes a hand piece 110, a proximal housing 120 situated above hand piece 110, a cannula 130 distally extending from proximal housing 120, and a trigger 140 distally extending from the housing 120. Each of the hand piece 110, housing 120, and/or cannula 130 may be disposable and/or reusable.

A top portion of housing 120 includes an open channel 111 configured to receive an endoscope 200 that is removably coupled to assembly 100. The endoscope 200 may be secured to housing 120 by i) threading the flexible endoscope shaft 220 through a hole or channel 114 extending from a distal end of channel 111 through a distal end of housing 120; and ii) securing the proximal endoscope head 210 within open channel 111. For example, the endoscope 200 may be slid into open channel 111 in a top-down manner. In this implementation, open channel 111 includes sidewalls 112 and tabs 113 extending from sidewalls 112. Sidewalls 112 may secure the sides of endoscope head 210, and tabs 113 may be bent to provide additional pressure against the sides of endoscope head 210 (e.g., to prevent it from sliding out). The material and thickness of tabs 113 may be tuned to optimize the force required to bend them into a suitable position.

Housing 120 may include some other removable attachment mechanism that enables removable attachment of an endoscope. For example, housing 120 may utilize a magnetic attachment mechanism, a snap on attachment mechanism, a top down ratchet mechanism, an insert ratchet mechanism, and/or an insert twist mechanism as further described in U.S. Pat. No. 10,512,391, incorporated herein by reference in its entirety. As such, it should be noted that the disclosure is not limited to the specific mechanisms described and illustrated herein for removably coupling endoscope 200, and that other mechanisms for removably coupling the endoscope 200 are contemplated. Additionally, although an endoscope 200 having a flexible (e.g., bendable) shaft 220 is described in the disclosure, in other implementations the assembly 100 may be adapted to receive an endoscope having a rigid shaft or a shaft that is part rigid and part flexible (hybrid). In some implementations, the endoscope shaft may be malleable, magnetic, hinged, detachable/removable, disposable, reusable, or permanently fixed to the endoscope housing 210.

Housing 120 may also include ports 121a and 121b respectively situated on left and right sides of housing 120. The ports 121a and 121b respectively couple to tubes 122a and 122b that may merge, in a "Y" type fashion, into a single hollow channel 122c passing through cannula 130, or alternatively, remain separate from one another as they pass independently through cannula 130. For example, port 121a may connect directly to the lumen of cannula 130 or to a proximal end of tube 122a, and port 121b may connect directly to the lumen of cannula 130 or to a proximal end of tube 122b. The tubes 122a and 122b may join to form tube 122c that terminates at the distal end of cannula 130, before the distal end of cannula 130, or after the distal end of cannula 130. Alternatively, the tubes 122a and 122b may separately terminate at the distal end of cannula 130, before the distal end of cannula 130, or after the distal end of cannula 130. Having the tubes separately terminate may provide the advantage of easing independent insertion and removal of flexible instruments via ports 121a and 121b. The cannula 130 may be rigid, malleable, flexible, or articulating and of adequate caliber to internally accommodate any combination of tubes 122a, 122b, and 122c. Various flexible instruments may be threaded or moved through ports 121a, 121b, and tubes 122a, 122b. For example, a balloon catheter, suction tool, micro-debrider, flexible drill, flexible injection needle, instrument tool or other articulating instrument may be advanced through the tubes 122a and 122b. Ports 121a and 121b might also be used for suction and irrigation purposes as might be required in orthopedic arthroscopy or urologic cases. Although ports 121a and 121b are incorporated in respective sides of housing 120, the ports may be placed in some other suitable location of housing 120. Alternatively, port holes, or a single port, may instead be placed on a proximal back end of housing 120 to permit instruments to be passed in a straight, linear fashion through the internal housing 120 and cannula 130. A back-end port location would be beneficial for passing rigid instruments through the cannula and may or may not require or involve separate tubes 122a or 122b terminating at or passing through cannula 130.

By virtue of the illustrated configuration, including ports 121a and 121b, the ergonomics of assembly 100 may be improved by allowing customization of ports 121a and 121b for various procedures. By having dual ports with separate tubes running into (and some implementations through) the cannula 130, a different instrument may be threaded through each tube in an order of preference of the physician. Additionally, the physician may choose from which direction (e.g., left, right, or back) to thread an instrument. In some implementations a third port hole may be placed in the housing (e.g., on a proximal back end of housing 120) and coupled to a third tube running into cannula 130 to permit instruments to be passed in a straight, linear fashion through the internal housing 120 and cannula 130).

Figure 6:
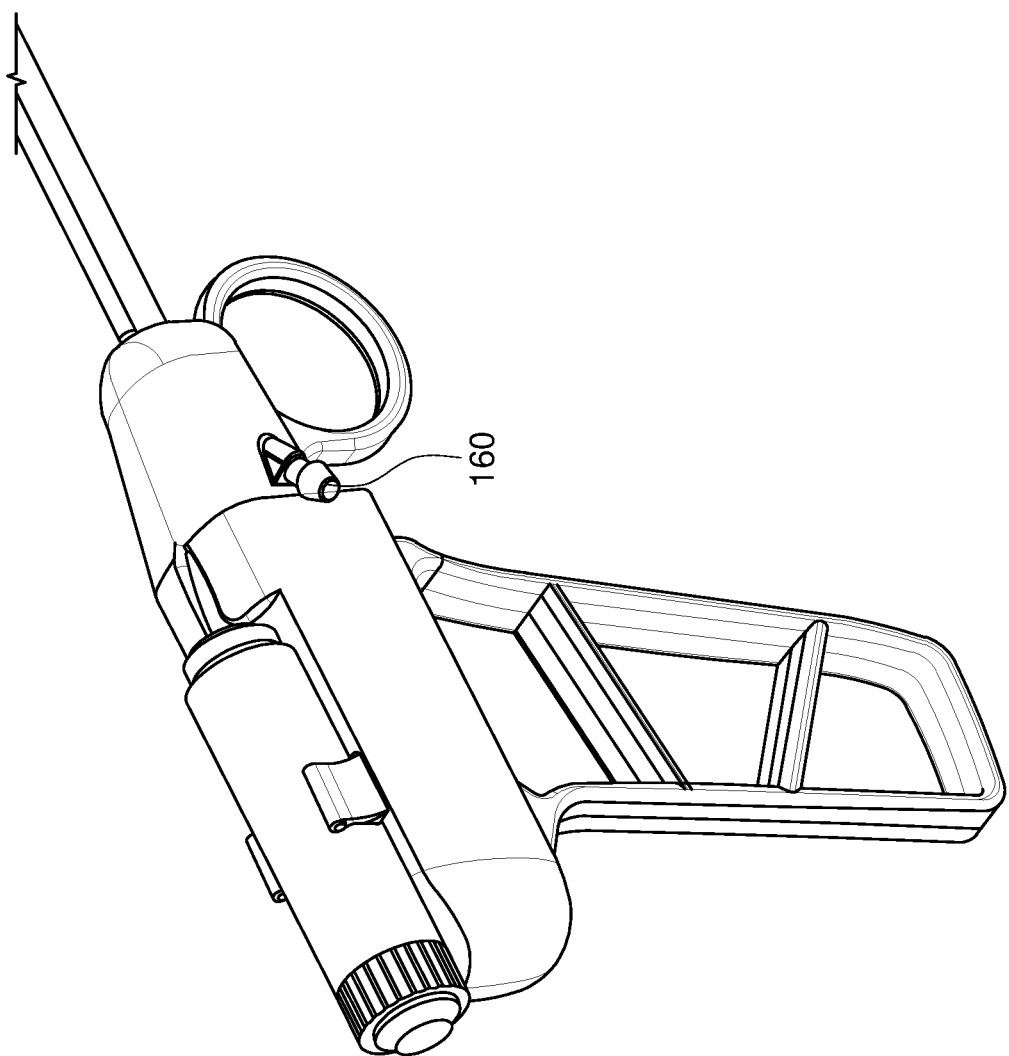
FIG. 6 shows a right side perspective view of the articulating cannula assembly of FIG. 5 with the suction adapter coupled to a port of the assembly.
Figure 7:
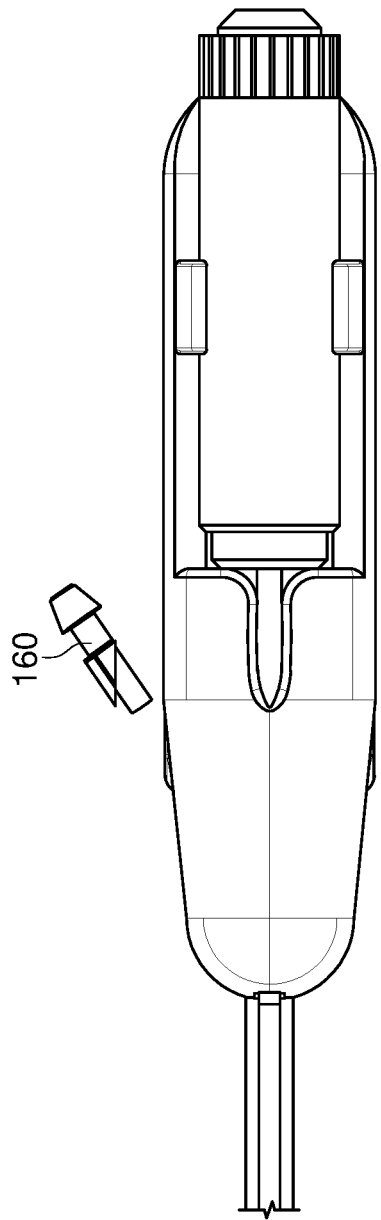
FIG. 7 shows a top view of an articulating cannula assembly with a coupled endoscope, including a suction adapter that can couple to a port of the assembly, in accordance with some implementations of the disclosure.
Figure 8:
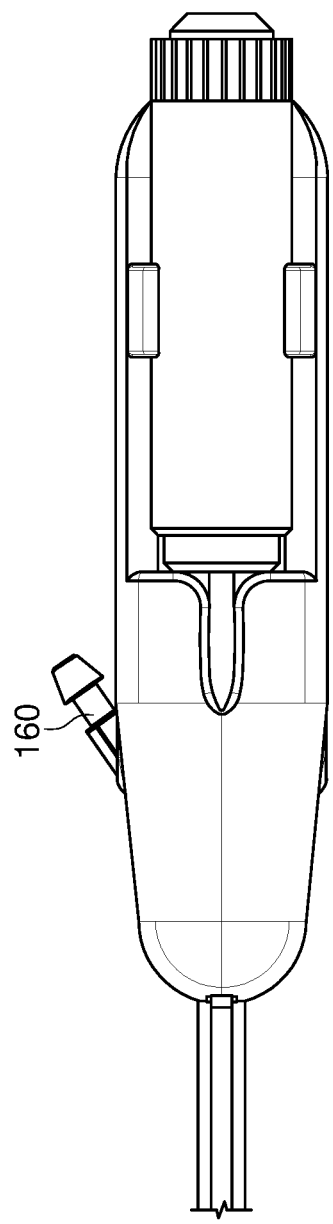
FIG. 8 shows a top side view of the articulating cannula assembly of FIG. 7 with the suction adapter coupled to a port of the assembly.
Figure 10:
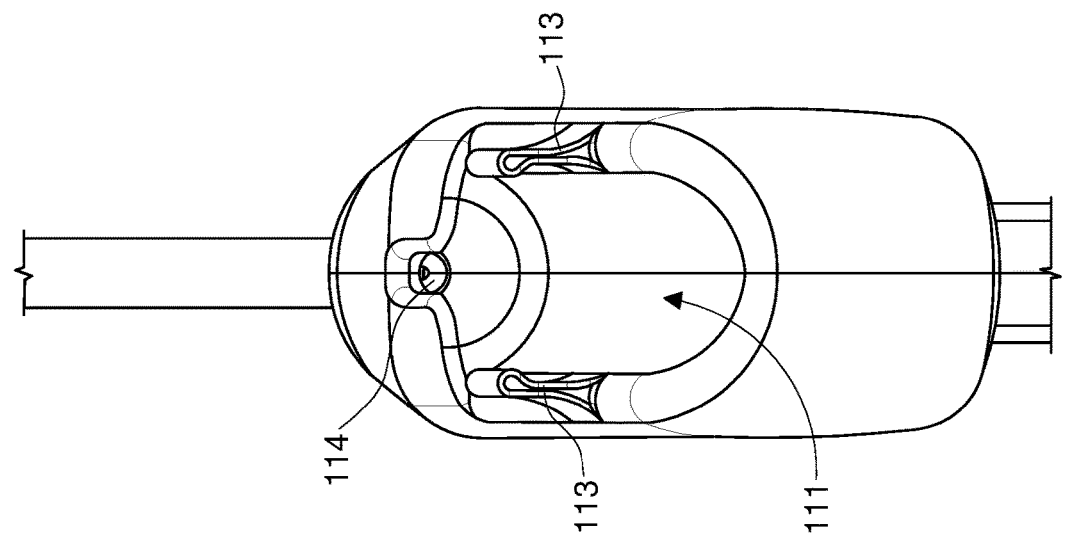
FIG. 10 shows a back and top side view of an articulating cannula assembly, without an endoscope coupled thereto, in accordance with some implementations of the disclosure.
Figure 9:
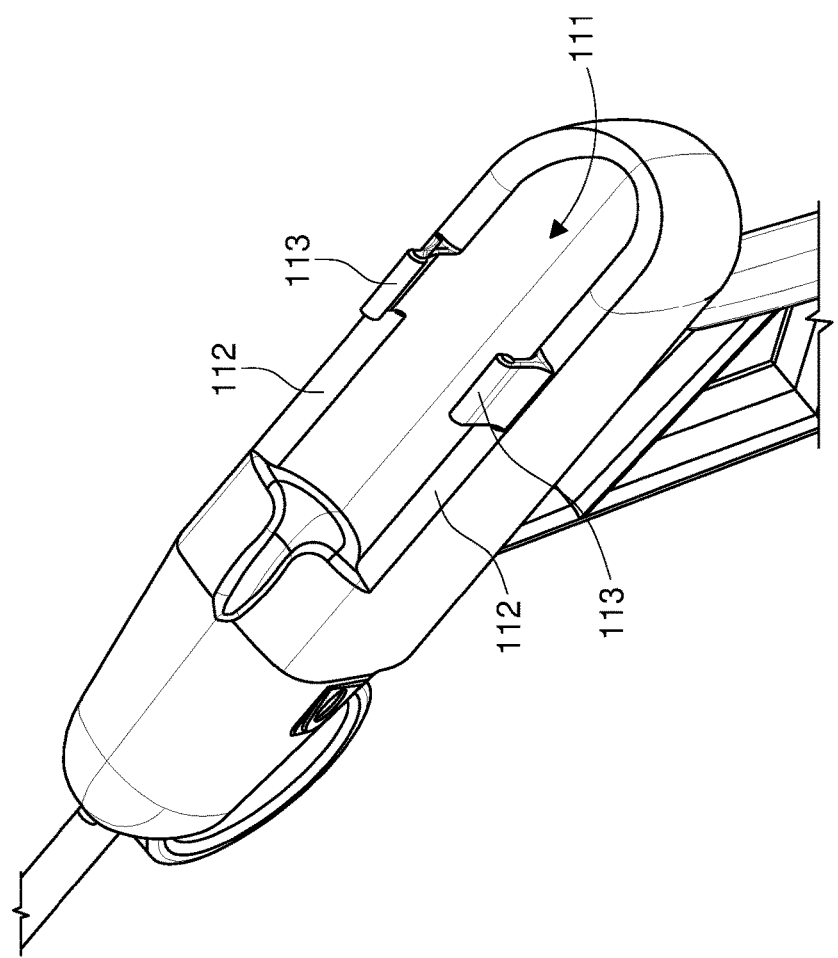
FIG. 9 shows a left side perspective view of an articulating cannula assembly, without an endoscope coupled thereto, in accordance with some implementations of the disclosure.

FIGS. 6-8 show a suction adapter 160 that can couple independently to either port 121a or 121b. The configuration of suction adapter 160 allows for it to receive and attach to the end of a suction hose. Suction adapter 160 would secure itself to the ports on housing 120 either with a pressure fit, threaded fit, snap fit, or other type of connector mechanism. Other types of adapters are envisioned that might couple to the side ports of assembly 100. Such adapters might include connectors to aid with securing instrumentation, irrigation, electrical (ex. cautery), pressure manometers, balloon catheters, guidewires, endoscopes, etc.

Figure 13:
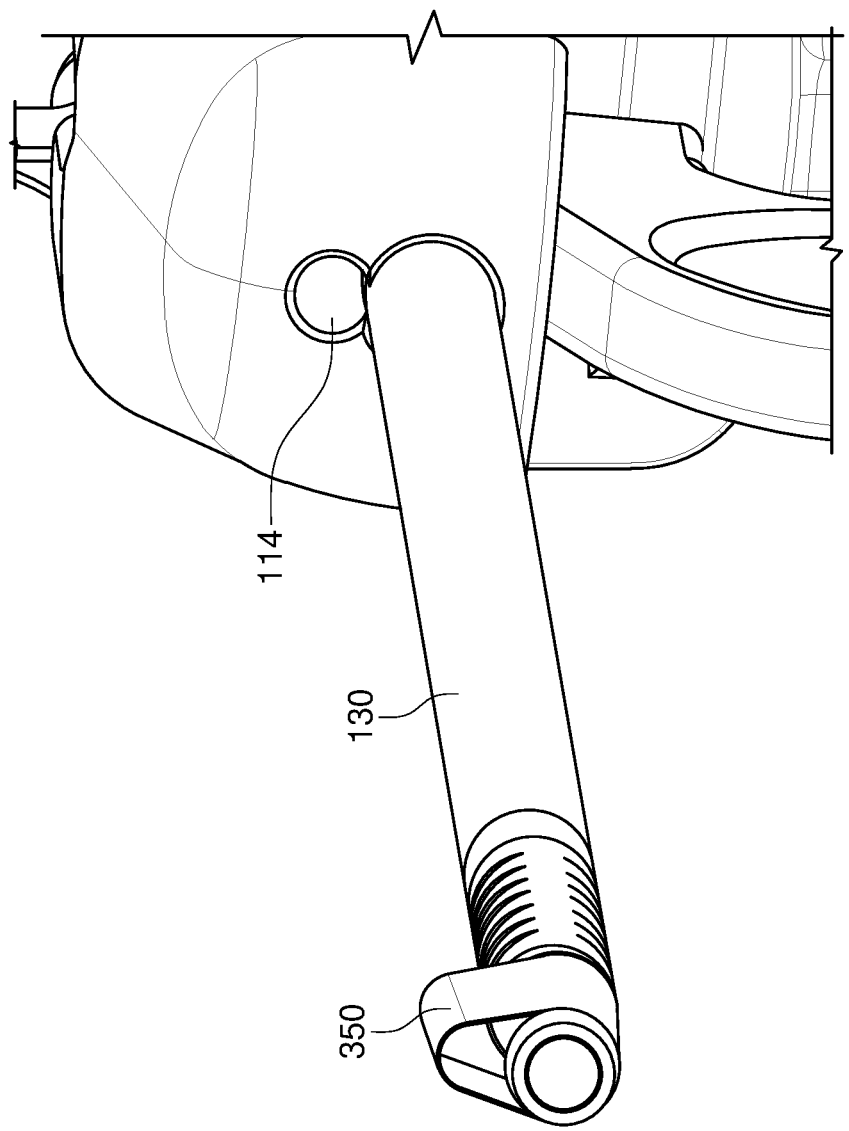
FIG. 13 shows a perspective view of a cannula of an articulating cannula assembly, a distal end of the cannula including a flexible band for securing a distal end of an endoscope shaft, in accordance with some implementations of the disclosure.
Figure 14:
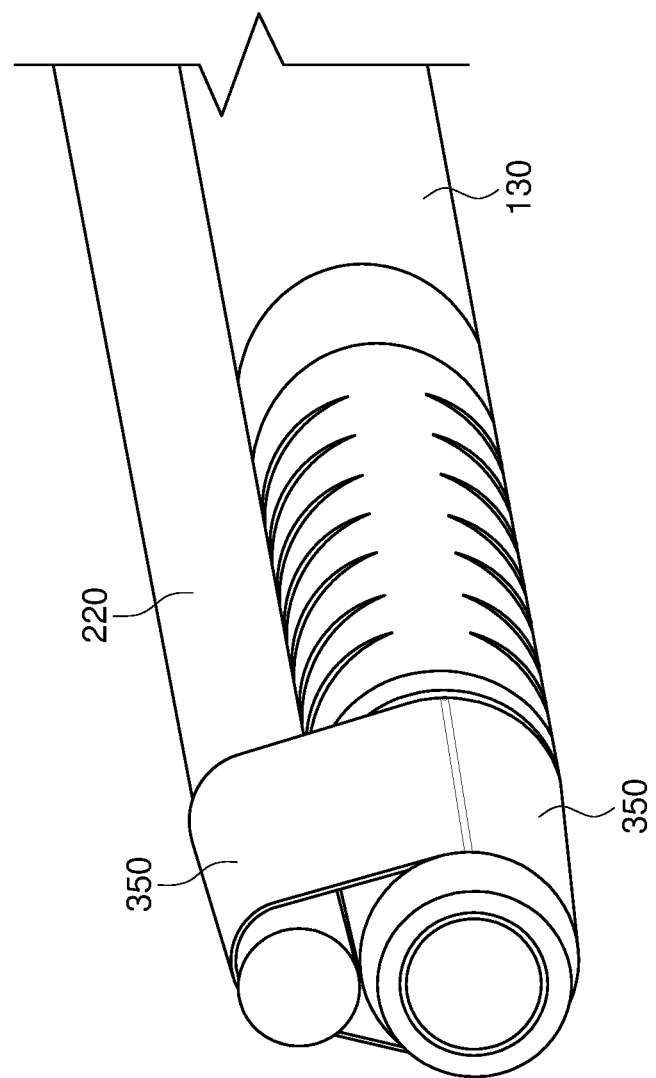
FIG. 14 shows a distal end of an endoscope shaft secured to the distal end of the cannula of FIG. 13 by the flexible band, in accordance with some implementations of the disclosure.
Figure 15:
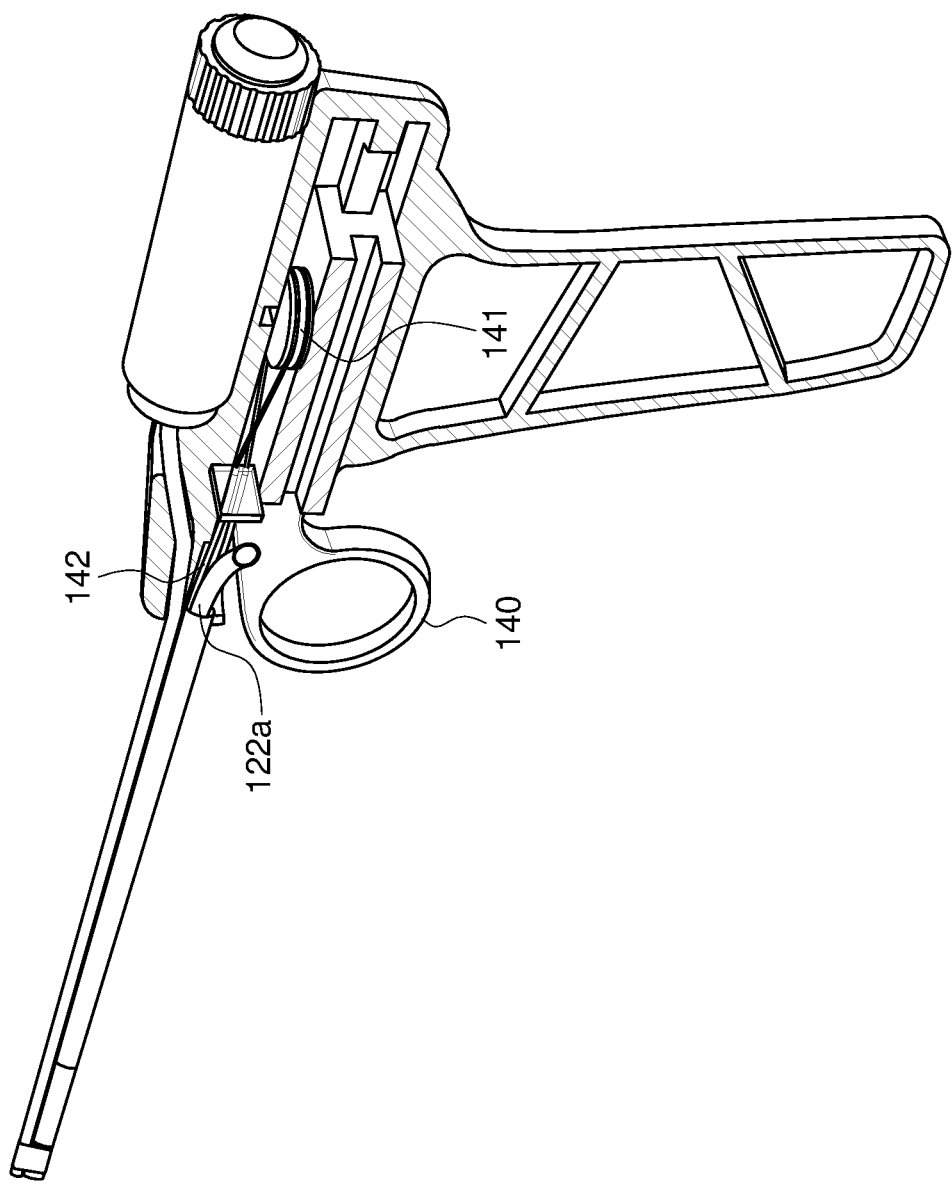
FIG. 15 shows an internal, left side perspective view of an articulating cannula assembly with a coupled endoscope, in accordance with some implementations of the disclosure.
Figure 16:
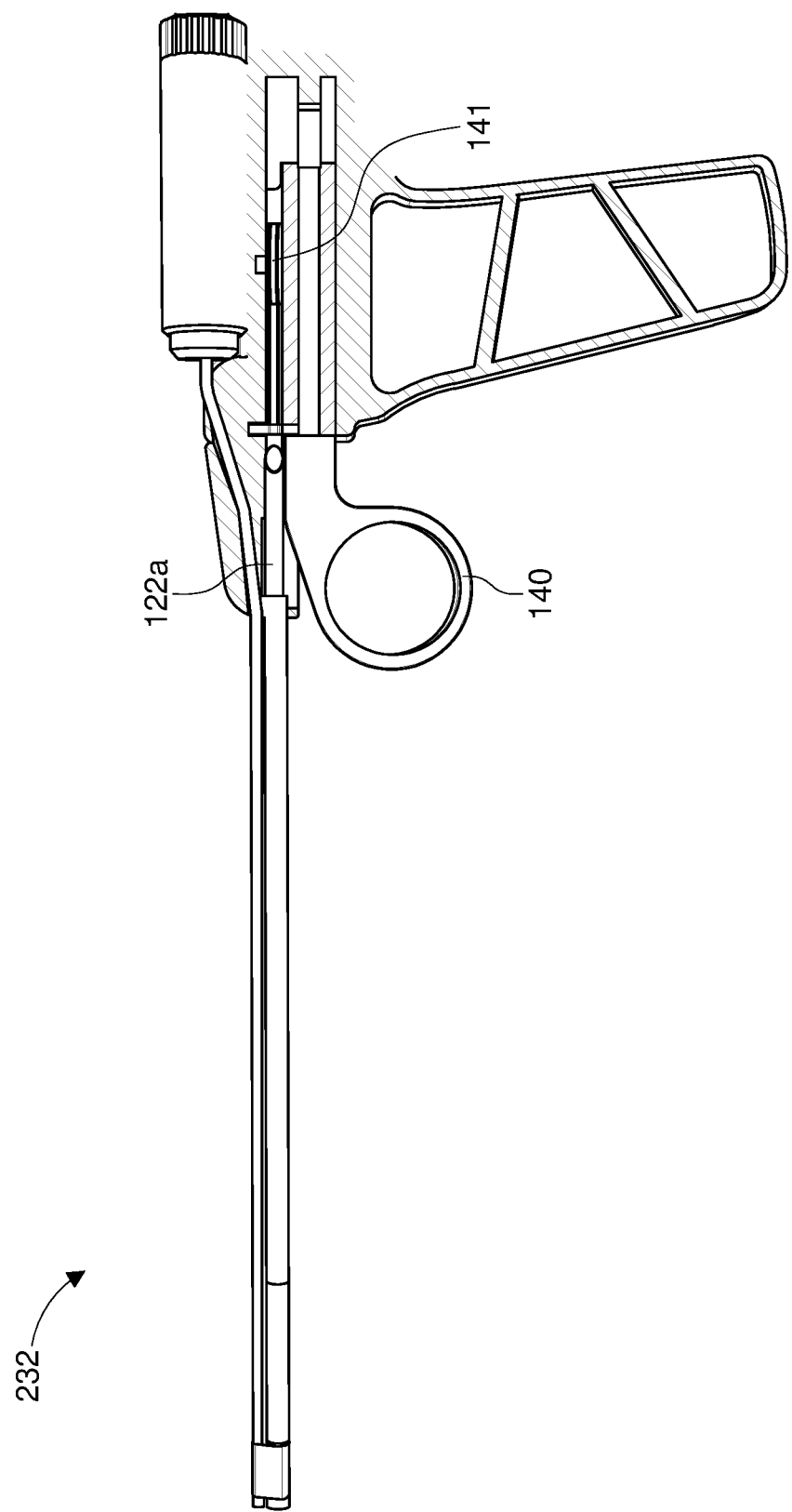
FIG. 16 shows an internal, left side perspective view of an articulating cannula assembly with a coupled endoscope, in accordance with some implementations of the disclosure.
Figure 17:
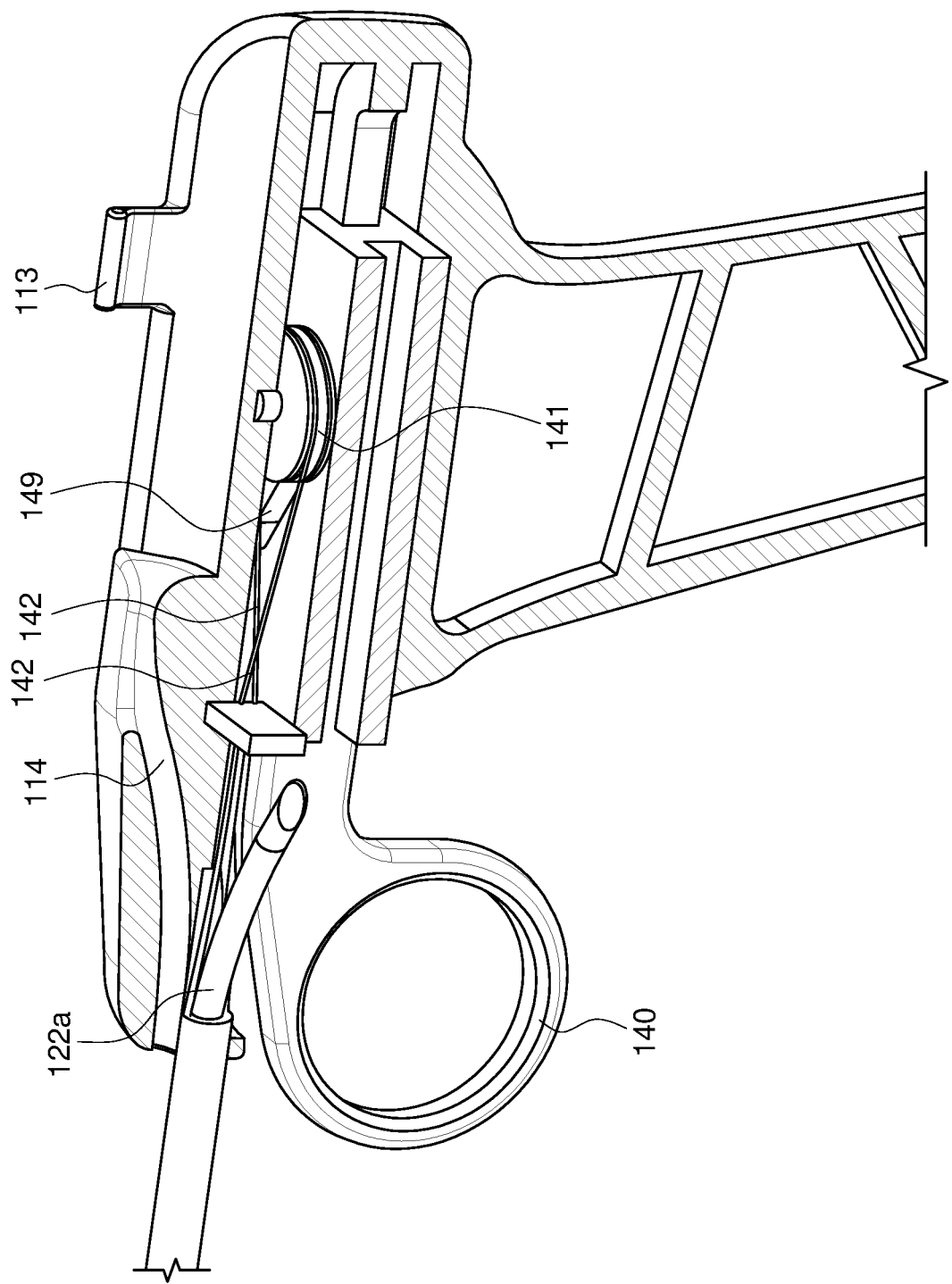
FIG. 17 shows an internal, left side perspective view of a proximal housing of an articulating cannula assembly, including a pulley mechanism contained therein, in accordance with some implementations of the disclosure.
Figure 18:
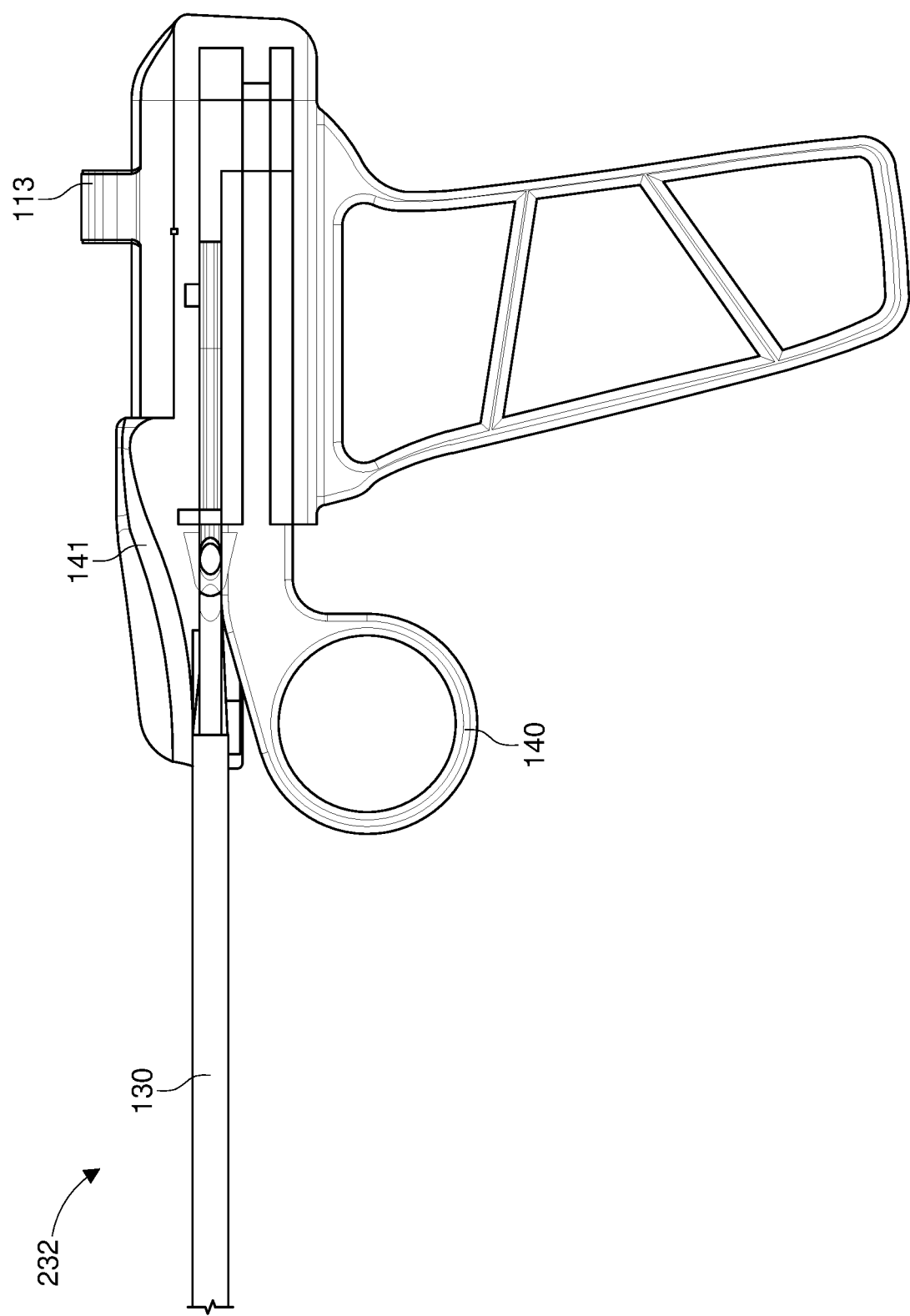
FIG. 18 shows an internal, left side view of a proximal housing of an articulating cannula assembly, in accordance with some implementations of the disclosure.
Figure 19:
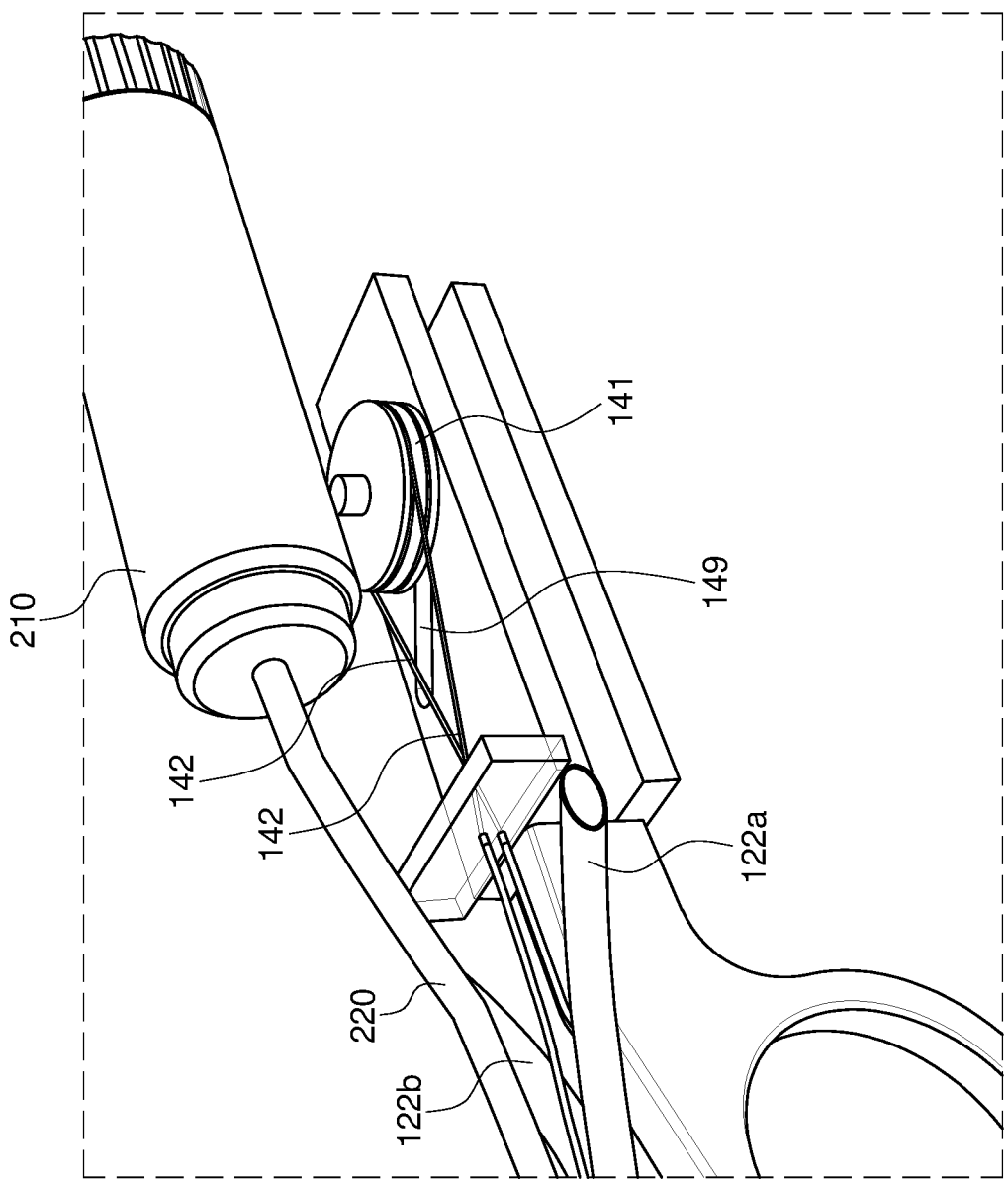
FIG. 19 shows an internal, perspective view of components contained within a proximal housing of an articulating cannula assembly, in accordance with some implementations of the disclosure.
Figure 20:
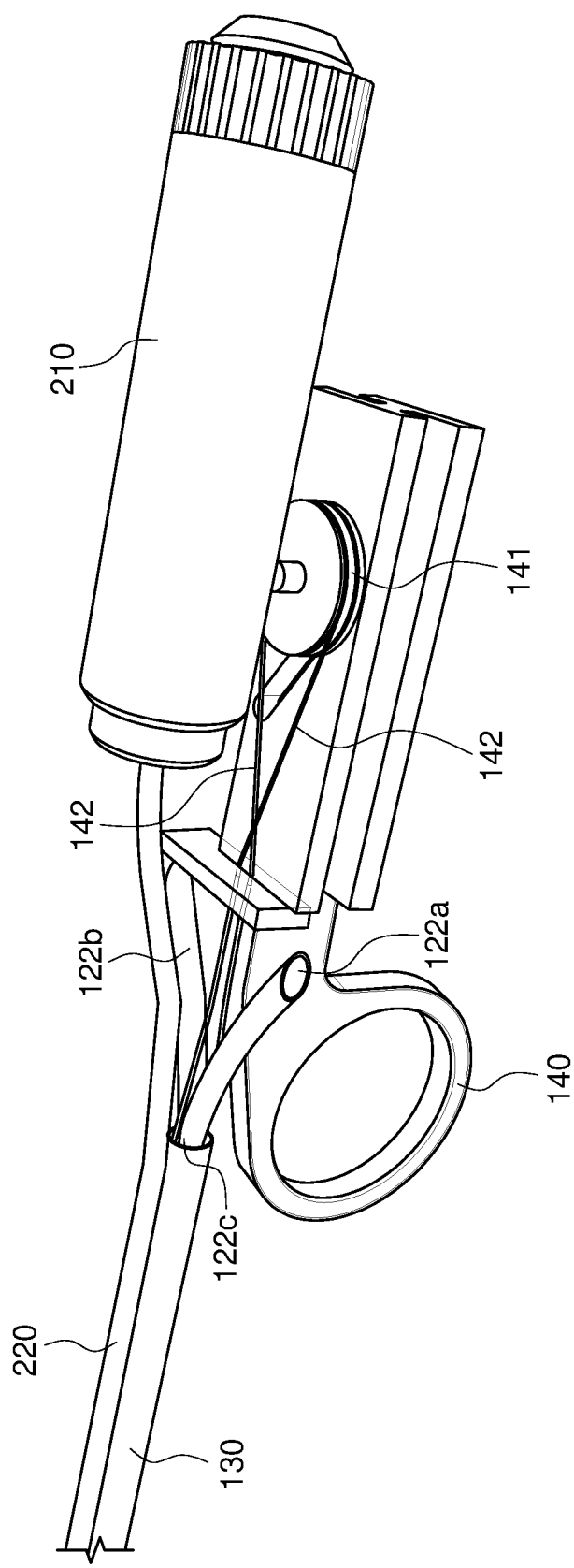
FIG. 20 shows an internal, perspective view of components contained within a proximal housing or cannula of an articulating cannula assembly, in accordance with some implementations of the disclosure.
Figure 21:
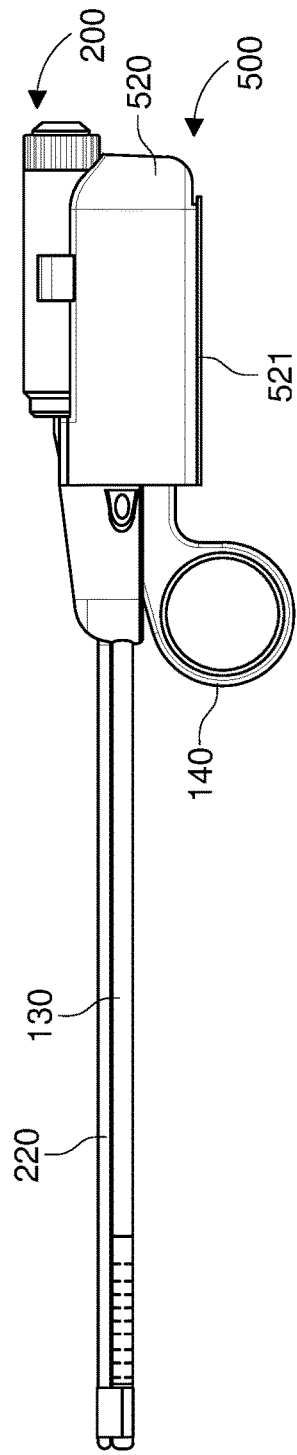
FIG. 21 shows a left side view of an articulating cannula assembly with a coupled endoscope, the assembly configured to be removably coupled to a hand piece, in accordance with some implementations of the disclosure.
Figure 22:
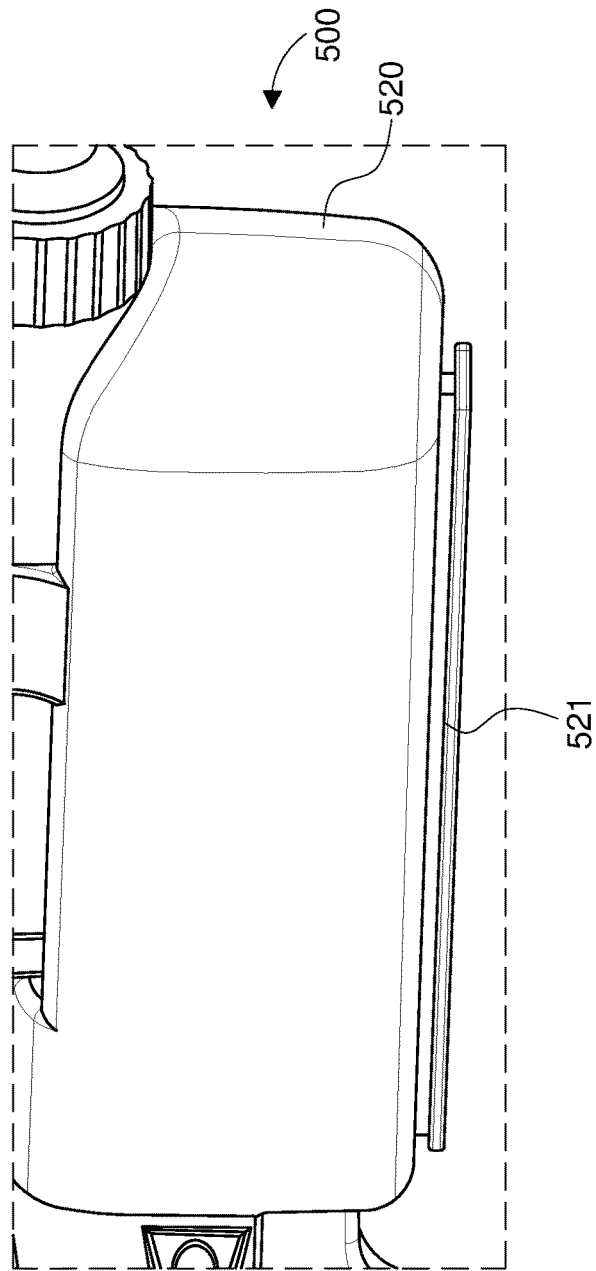
FIG. 22 shows a T-shaped attachment structure of a housing of the articulating cannula assembly of FIG. 21, the attachment structure configured to slide into a T-track of a hand piece, in accordance with some implementations of the disclosure.
Figure 24:
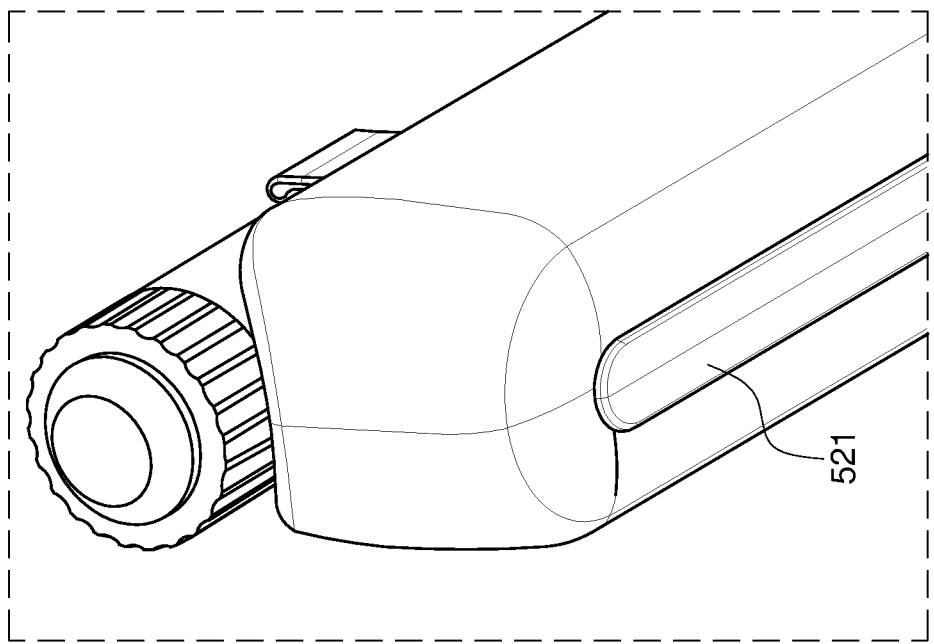
FIG. 24 shows a back and bottom side view of the articulating cannula assembly of FIG. 21.
Figure 23:
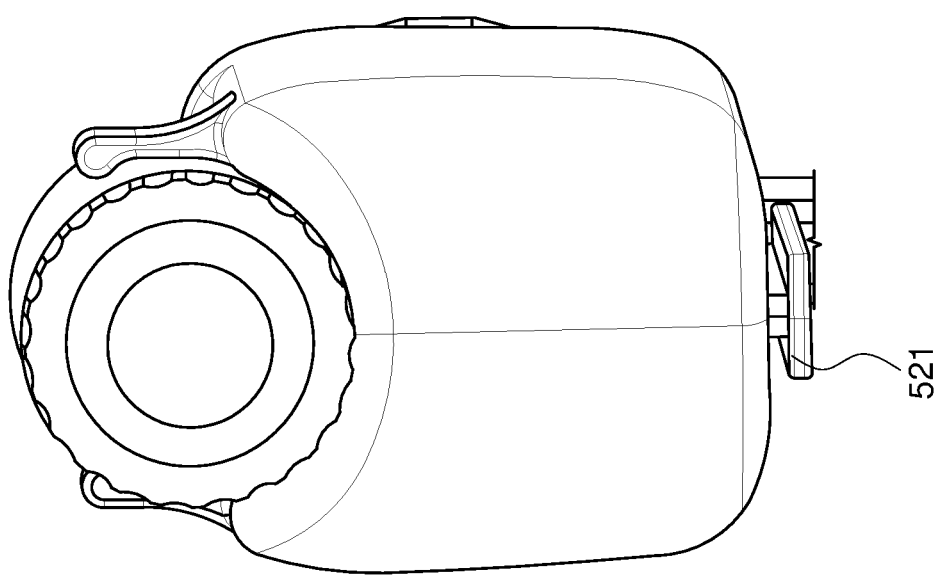
FIG. 23 shows a back side view of the articulating cannula assembly of FIG. 21.

As depicted by FIGS. 11-13, a distal end of endoscope shaft 220 may be secured to a distal end of cannula 130 via a flexible band 350. In some implementations, the flexible band 350 may be integrated into the distal end of cannula 130. Alternatively, the flexible band 350 can be a separate component. Although the illustrated examples show a flexible band 350 for securing endoscope shaft 220 to cannula 130, other attachment mechanisms may be used. For example, in some implementations the cannula 130 may incorporate an additional channel outside of the interior tube for guiding and/or removably coupling to endoscope shaft 220. The additional channel may run parallel to the cannula 130, and it may be open or closed, flexible or rigid. Further example mechanisms for attaching an endoscope shaft 220 to a cannula 130 or other tool can include single or multiple clips, tubes, wire loops, flexible open channels, slidable tracts, clamps, magnets, suction, and adhesives, some of which are described in U.S. Pat. No. 10,512,391, incorporated herein by reference in its entirety.

In some implementations, to provide additional flexibility in imaging a patient's cavity at different angles, a segment 138 of cannula 130 containing the flexible band 350 (or other distal endoscope attachment mechanism) and extending beyond the articulating segment 135 of cannula 130, may be rotatable, independent of the rest of the cannula 130. As depicted by the arrow in FIG. 11, The segment 138 can rotate along with the coupled tip/distal end of endoscope shaft 220, thereby enabling imaging at different angles/orientations. To enable such rotation, the endoscope shaft 220 can be flexible.

With reference now to the articulating mechanism of articulating cannula assembly 100, the cannula 130 is illustrated in FIGS. 11-12 as having an articulating segment 135. The articulating segment 135 includes multiple notches 136 that widen or close depending on how trigger 140 is actuated (e.g., pulled or released). To enable this action, wires 142 extend from articulating segment to a pulley 141 incorporated into housing 120. Depending on how trigger 140 is actuated, the pulley 141 can be configured to rotate (e.g., clockwise/counterclockwise), translate along a surface (e.g., move laterally along the plane it is on), or some combination thereof. For example, in one particular implementation depicted by FIGS. 17 and 19, the pulley may rotate while it moves forward or backward along channel 149. In one embodiment, trigger 140 may be in the shape of a ring located along the undersurface of articulating cannula assembly 100. In other embodiments, the articulating segment 135 may be actuated by a trigger located elsewhere along the surface of the articulating cannula assembly 100, such as on the either side of the housing. The trigger may be in the form of a ring, lever, button, dial, or electrical connector.

It should be noted that although articulating segment 135 is shown near the distal end of cannula 130, it may be implemented closer to the proximal end of cannula 135. In some implementations, there may be multiple articulating segments along the cannula 130 operated by one or multiple triggers or similar type actuating mechanisms.

In some implementations, a flexible coating 137 may cover articulating segment 135, including notches 136 such that gaps aren't exposed during articulation. The flexible coating 137 may be removable or a permanent part of cannula 130. In some implementations, the part of cannula 130 distal to the articulating segment 135 may be rotatable.

In some implementations, the cannula 130 and/or the hand piece 110 may be integrated with housing 120 as illustrated in the example of FIGS. 1-20. In other implementations, the cannula and/or the hand piece may be removably coupled to the housing 120. In such implementations, the removable connection may be made via press fitting, snap fitting, friction fitting, magnetic coupling, clamps, threaded turns, one or more dovetails, or some other suitable mechanism. By virtue of a removable hand piece connection, the housing 120 may be utilized with different hand pieces, including a balloon pump hand piece, further discussed below with respect to FIG. 27, or an alternative type handpiece such as, but not limited to, an irrigation syringe, injection syringe, motorized handpiece, endoscopic enabled handpiece, etc. For example, FIGS. 21-24 illustrate an articulating cannula assembly 500 having a housing 520 configured to be removably coupled to a hand piece. In this example, a lower portion of housing 520 includes a T-shaped attachment structure 521 configured to slide into a T-track of a hand piece. The T-track may be incorporated into a top portion of the hand piece. A releasable lever or some other suitable mechanism, not pictured, could secure the handpiece to the articulating cannula assembly in a reversible manner.

Figure 25:
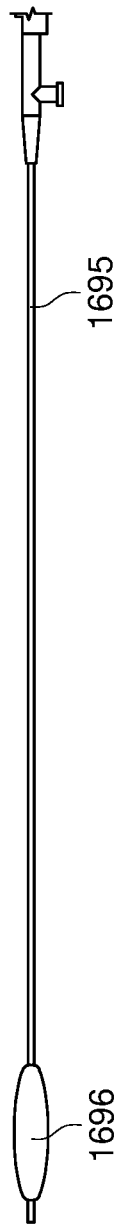
FIG. 25 shows a flexible balloon catheter that can be used with an articulating cannula assembly, in accordance with some implementations of the disclosure.

FIG. 25 illustrates an example flexible balloon catheter 1695 that may be used with assembly 100. The flexible balloon catheter 1695 may be particularly suited for esophageal dilation. Patients who have difficulty swallowing secondary to cervical esophageal stricture or chronic cricopharyngeal spasm often require esophageal dilatation. Esophageal dilatation is rarely performed in the office setting and is almost always performed by gastroenterologists under sedative anesthesia. Esophageal dilatation is usually performed at the same time as esophagogastroduodenoscopy (EGD). Although EGD is sometimes necessary, it is not required every time a patient requires dilation. This is especially true for patients requiring multiple dilatations over time as might occur following radiation therapy or related to chronic laryngopharyngeal reflux. Current techniques for esophageal dilatation may involve serial dilation with progressively sized Bougie catheters and esophageal balloon catheters.

The flexible balloon catheter 1695 has on its distal end an inflatable balloon 1696. When the balloon 1696 is in a non-inflated state, the balloon catheter 1695 may be inserted through port 121a or 121b, and advanced through hollow tube 122a or hollow tube 122b. The flexible balloon catheter 1695 may be of sufficient length to allow extension of the balloon beyond the distal end of the cannula 130. The esophageal balloon catheter may itself have a hollow core around which the balloon is fixated and through which a small guidewire could be inserted. During an operation, the endoscope 200 may be used to visualize the balloon 1696, balloon catheter 1695, and in some instances a balloon catheter guidewire as it passes from the distal end of the cannula 130 into the cervical esophagus. A small marking on the catheter proximal to the balloon 1696 may be used to help endoscopically approximate the proper distance to insert the catheter 1695 into the esophagus prior to balloon inflation. The illustrated system may allow for simple, low cost, safe, and effective cervical balloon esophageal dilatation that could be performed in the office setting, under endoscopic guidance, and without the need for anesthesia or accompanying EGD procedure. Such an implementation could be used trans-nasally or trans-orally to achieve a similar result depending on patient anatomy and tolerance to the procedure.

Figure 26:
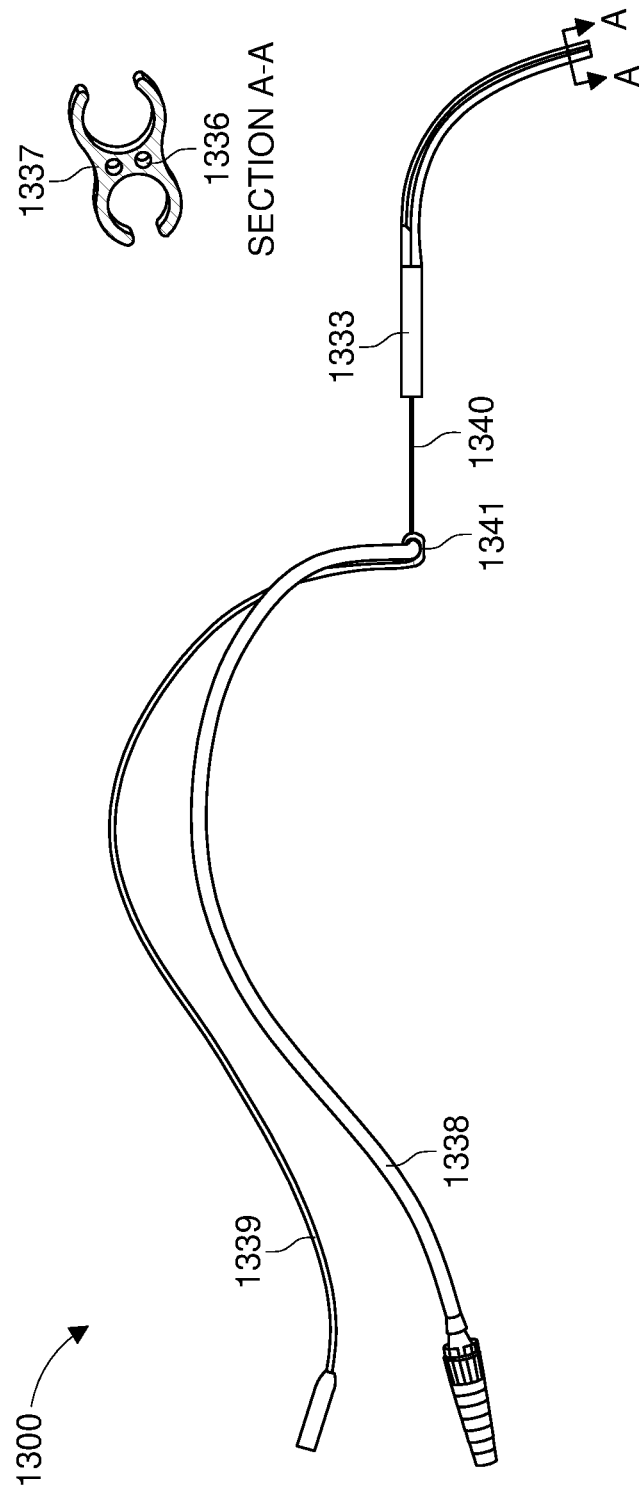
FIG. 26 shows a suction line and irrigation line assembly that can be used with an articulating cannula assembly, in accordance with some implementations of the disclosure.

FIG. 26 shows a suction line and irrigation line assembly 1300 that may be used with assembly 100. The assembly 1300 includes a suction line 1338 and irrigation line 1339 that may attach proximally to a detachable insert 1333. To minimize excess lines and entanglement, the irrigation and suction lines 1338, 1339 converge at junction 1341 into a smaller caliper dual line 1340 that acts as one line extending from the detachable insert 1333 to point away from the hand piece 110. Within the wall of insert 1333, there may be incorporated one or more hollow channels through which suction 1336 or irrigation 1337 could be delivered to the distal endoscope, lens, or instrument tool component. The assembly 1300 may be applied externally to cannula 130 via a dual, open channel scope/cannula attachment mechanism (FIGS. 25-26, Section A-A). Alternatively, a different implementation of 1300 without the dual scope/cannula attachment channels, and only the irrigation and suction channels, could be inserted through port 121a or 121b, and advanced through hollow tube 122a or hollow tube 122b to converge or pass independently through the hollow extension of the distal end of assembly 1300 (e.g., section A-A) to a point at or beyond the distal end of the cannula 130.

Figure 27:
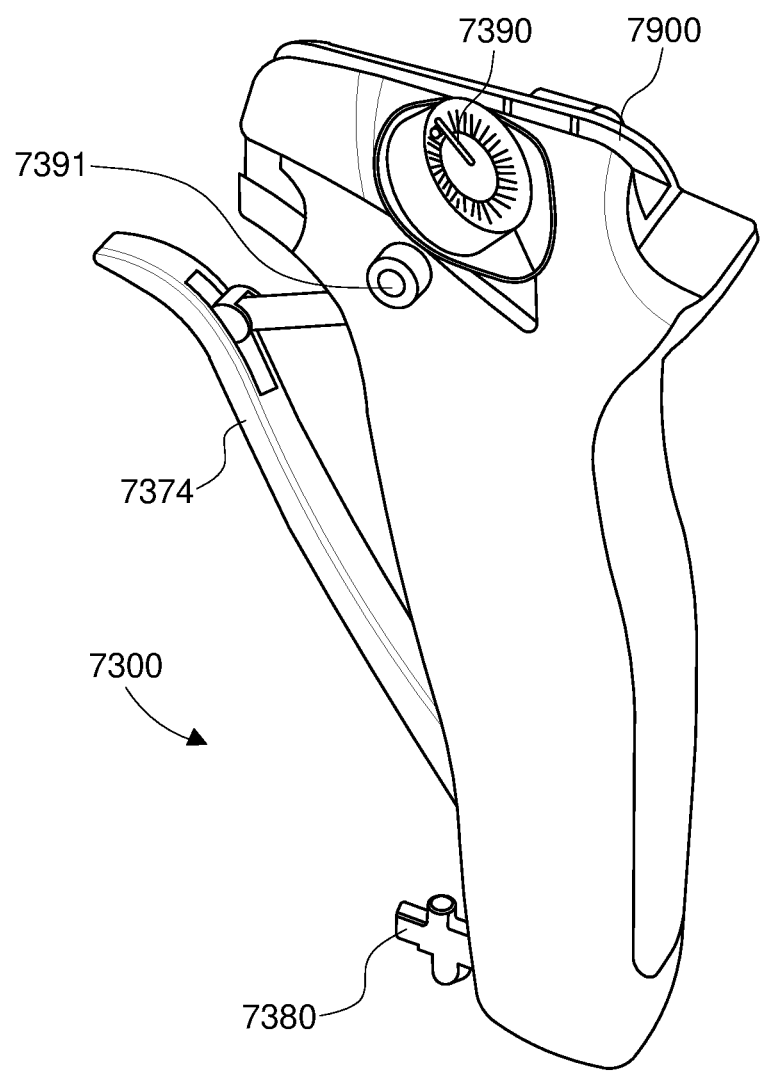
FIG. 27 shows a balloon pump hand piece that the articulating cannula assembly of FIG. 21 can removably couple to, in accordance with some implementations of the disclosure.

FIG. 27 depicts a balloon pump hand piece 7300 that an articulating cannula assembly 500 may removably couple to via an attachment structure 521 of housing 520, in accordance with implementations of the disclosure. For example, attachment structure may be slidably coupled to channel 7900 located at a top end of hand piece 7300. Although channel 7900 is depicted as an open channel that the structure 521 attaches to in this example, the channel may incorporate any suitable mechanism for removably coupling to the housing 520.

The balloon pump hand piece 7300 includes a pump handle 7374 that, when actuated, pumps pressurized air or liquid (e.g., water or saline) through a balloon connection port 7380 and into the connected, proximal end of a flexible balloon catheter 1695. The balloon connection port 7380 may be located along the base of the balloon pump hand piece or at some other location along the surface of hand piece 7300. The uninflated distal balloon could then be inserted in port 121a or 121b and through cannula 130). When the balloon is ultimately inflated, pressure may be measured by a pressure gauge 7390 incorporated into the balloon pump hand piece 7300. The balloon pump hand piece 7300 also includes a button 7391 that, when actuated, may release the pressure from the distal balloon.

The pressurized fluid may be stored in a chamber (not shown) incorporated into the balloon pump hand piece 7300. In some implementations, the chamber is a fluid syringe that may snap into the body of the handle, or the syringe may be part of the handle. The chamber may be removable. The chamber may be prefilled or refillable via port 7380 or via another port located separately on the hand piece.

Although described above in terms of various example implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation. Thus, the breadth and scope of the present application should not be limited by any of the above-described example implementations.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide some instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. An articulating cannula assembly, comprising:
a hand piece;
a proximal housing situated above the hand piece;
a trigger;
a pulley configured to rotate or translate when the trigger is actuated;
a cannula distally extending from the proximal housing, the cannula comprising an articulating segment including multiple notches; and
one or more wires coupling the articulating segment to the pulley,
wherein the trigger is configured such that, when actuated, it extends or contracts the articulating segment by causing the multiple notches to widen or close.

2. The articulating cannula assembly of claim 1, wherein the proximal housing is configured to removably couple to the hand piece.

3. The articulating cannula assembly of claim 2, wherein:
the hand piece is a balloon pump hand piece comprising a connection port configured to fluidically couple to a balloon catheter;
the balloon pump handpiece comprises a control configured to inflate a distal balloon of the balloon catheter; and
a top portion of the balloon pump hand piece comprises a mechanism configured to removably couple to the proximal housing.

4. The articulating cannula assembly of claim 3, wherein:
the proximal housing comprises a port that connects to the cannula;
the port is configured to receive the distal balloon of the balloon catheter; and
the distal balloon is configured to be passed through the cannula.

5. The articulating cannula assembly of claim 2, wherein:
one of the hand piece or the proximal housing comprises a T-shaped attachment structure;
the other of the hand piece or the proximal housing comprises a T-track; and
the hand piece is configured to be removably coupled to the proximal housing by sliding the T-shaped attachment structure in the T-track.

6. The articulating cannula assembly of claim 2, wherein a bottom portion of the proximal housing includes a coupling mechanism configured to press fit, snap fit, friction fit, or magnetically attach to a top portion of the hand piece.

7. The articulating cannula assembly of claim 1, wherein:
the proximal housing comprises a first port and a second port that connect to the cannula; and
the first port is configured to receive a first instrument that is passed through the cannula; and
the second port is configured to receive a second instrument that is passed through the cannula.

8. The articulating cannula assembly of claim 7, further comprising:
a first tube that connects the first port to the cannula, and passes through at least a portion of the cannula; and
a second tube that connects the second port to the cannula, and passes through at least a portion of the cannula,
wherein the first instrument is configured to be passed through the first tube, and the second instrument is configured to be passed through the second tube.

9. The articulating cannula assembly of claim 8, wherein the first tube and the second tube separately terminate within the cannula or after a distal end of the cannula.

10. The articulating cannula assembly of claim 8, wherein the first tube and the second tube merge into a single channel within the cannula.

11. The articulating cannula assembly of claim 7, wherein the first port and the second port are situated on opposite sides of the proximal housing.

12. The articulating cannula assembly of claim 11, wherein:
the proximal housing comprises a third port that connects to the cannula, the third port configured to receive a third instrument that is passed through the cannula,
the first port and the second port are situated on left and right sides of the proximal housing, and the third port is situated on a rear side of the proximal housing.

13. The articulating cannula assembly of claim 1, wherein the proximal housing comprises a first port that connects to the cannula, the first port situated on a rear side of the proximal housing and configured to receive one or more instruments that are passed through the cannula.

14. The articulating cannula assembly of claim 13, wherein the articulating segment comprises a flexible coating disposed over the multiple notches.

15. The articulating cannula assembly of claim 1, wherein the cannula further comprises a rotatable segment distal to the articulating segment, the rotatable segment configured to rotate independent of a remainder of the cannula.

16. The articulating cannula assembly of claim 1, wherein the proximal housing comprises a first endoscope attachment structure for removably securing a proximal portion of an endoscope.

17. The articulating cannula assembly of claim 16, wherein:
the first endoscope attachment structure comprises an open channel with side walls and a distal hole that extends from a distal end of the open channel to a distal end of the proximal housing; and
the endoscope is configured to be removably secured to the first endoscope attachment structure by threading a shaft of the endoscope through the distal hole and securing the proximal portion of the endoscope within the open channel.

18. The articulating cannula assembly of claim 16, further comprising: a second endoscope attachment structure for securing an exterior of the cannula to a shaft of the endoscope.

19. The articulating cannula assembly of claim 18, wherein the second endoscope attachment structure is incorporated into a distal portion of the cannula.

20. The articulating cannula assembly of claim 18, wherein the cannula further comprises a rotatable segment distal to the articulating segment, the rotatable segment comprising the second endoscope attachment structure, and the rotatable segment configured to rotate independent of a remainder of the cannula.

* * * * *